(12) United States Patent
Cattuzzato et al.

(10) Patent No.: US 11,224,627 B2
(45) Date of Patent: Jan. 18, 2022

(54) **METHOD FOR CULTURING CELLS OF *ACROCHAETIUM MONILIFORME* RED ALGAE, METHOD FOR OBTAINING AN EXTRACT OF THE BIOMASS THEREOF, AND USE OF SAME IN COSMETICS**

(71) Applicants: SOCIETE D'EXPLOITATION DE PRODUITS POUR LES INDUSTRIES CHIMIQUES SEPPIC, Paris (FR); BIOTECHMARINE, Quemper Guezennec (FR)

(72) Inventors: Laetitia Cattuzzato, Castres (FR); Erwan Le Gelebart, Quemper Guezennec (FR)

(73) Assignees: SOCIETE D'EXPLOITATION DE PRODUITS POUR LES INDUSTRIES CHIMIQUES SEPPIC, Paris (FR); BIOTECHMARINE, Quemper Guezennec (FR)

( * ) Notice: Subject to any disclaimer, the term of this patent is extended or adjusted under 35 U.S.C. 154(b) by 401 days.

(21) Appl. No.: 15/564,624

(22) PCT Filed: Apr. 8, 2016

(86) PCT No.: PCT/FR2016/050816
§ 371 (c)(1),
(2) Date: Oct. 5, 2017

(87) PCT Pub. No.: WO2016/162648
PCT Pub. Date: Oct. 13, 2016

(65) Prior Publication Data
US 2018/0117106 A1 May 3, 2018

(51) Int. Cl.
*A61K 36/02* (2006.01)
*A01G 33/00* (2006.01)
*C12N 1/12* (2006.01)
*A61P 17/00* (2006.01)

(52) U.S. Cl.
CPC .............. *A61K 36/02* (2013.01); *A01G 33/00* (2013.01); *A61P 17/00* (2018.01); *C12N 1/12* (2013.01); *Y02A 40/80* (2018.01)

(58) Field of Classification Search
CPC ................................................... A61K 36/02
See application file for complete search history.

(56) References Cited

U.S. PATENT DOCUMENTS

2007/0134783 A1   6/2007   Kakita et al.

FOREIGN PATENT DOCUMENTS

| CN | 102475664 A | 5/2012 | |
| CN | 102525864 A | 7/2012 | |
| CN | 103858745 A | 6/2014 | |
| CN | 103931482 A | 7/2014 | |
| EP | 2036537 A1 * | 3/2009 | ............. A61Q 19/00 |
| EP | 1 515 688 B1 | 7/2013 | |
| FR | 2 911 278 A1 | 7/2008 | |
| JP | 09301821 A * | 11/1997 | |
| JP | 2002-193736 A | 7/2002 | |
| JP | 2005-047910 A | 5/2005 | |
| KR | 10-2007-0089309 A | 8/2007 | |
| KR | 10-1409764 B1 | 6/2014 | |
| WO | 96/00719 A1 | 1/1996 | |
| WO | 2008/046791 A1 | 4/2008 | |

OTHER PUBLICATIONS

"WoRMS Rhodochorton moniliforme". Naming date: Drew, 1928. [Retrieved from the Internet on Jan. 4, 2020], Retrieved from: <URL: http://www.marinespecies.org/aphia.php?p=taxdetails&id=144372>. (Year: 1928).*
"WoRMS Rhodochorton". Upated on: Jul. 4, 2012. [Retrieved from the Internet on: Jan. 4, 2020], Retrieved from: <URL: http://www.marinespecies.org/aphia.php?p=taxdetails&id=143801>. (Year: 2012).*
Office Action issued in Chinese Patent Application No. 201680028349.3 dated Mar. 18, 2020 with English translation provided.
Office Action issued in Japanese Patent Application No. 2017-552969 dated Aug. 11, 2020 with English translation provided.
Stegenga, H. and Mulder, A.S., "Remarks on the *Audouinella microscopica* (Nag) Woelkerling Complex, With a Brief Survey of the Genus *Chromastrum papenfuss* (Rhodophyta, Nemaliales)," Acta Bot. Neerl. 28(4/5), Aug. 1979, p. 289-311.
Office Action issued in Chinese Patent Application No. 201680028349.3 dated Dec. 29, 2020 with English translation provided.
"Marine Biotechnology," edited by Chengkui Zeng et al., Shandong Science and Technology Press, Dec. 31, 1998, pp. 7-12 English concise statement of relevance listed in Chinese Office Action.
Chato-Salvador et al., "Non-enzymatic isolation of somatic cells from Kappaphycus spp. and Eucheuma denticulatum (Solieriaceae, Rhodophyta)," European Journal of Phycology, vol. 49, No. 4, 2014, pp. 486-492.

(Continued)

*Primary Examiner* — Amy L Clark
(74) *Attorney, Agent, or Firm* — Nixon & Vanderhye

(57) ABSTRACT

Disclosed is a method for obtaining a unialgal biomass of cells of small multicellular macroalgae, including: preparing a unialgal sample of cells of multicellular macroalgae from a sample of microalgae taken from the natural environment; culturing the unialgal sample of cells of multicellular macroalgae obtained in step in sea water to which at least one nitrogen source is added, in order to obtain an aqueous suspension of the unialgal biomass of cells of small multicellular macroalgae; a step of harvesting the unialgal biomass of cells of small multicellular macroalgae from the aqueous suspension obtained at the end of step; and a step of producing a powder of the unialgal biomass of cells of small multicellular macroalgae obtained in step. Also disclosed is glycolic extract of the aforementioned biomass, to a method for producing the extract, to the use thereof in cosmetics and pharmaceuticals, and to compositions containing same.

4 Claims, No Drawings

(56) References Cited

OTHER PUBLICATIONS

Cruz-Uribe et al., "Uptake and Biotransformation of 2,4,6-Trinitrotoluene (TNT) by Microplantlet Suspension Culture of the Marine Red Macroalga Portieria hornemannii," Biotechnology and Bioengineering, vol. 93, No. 3, Feb. 20, 2006, pp. 401-412.

Dawes et al., "Branch, micropropagule and tissue culture of the red algae Eucheuma denticulatum and Kappaphycus alvarezii farmed in the Philippines," Journal of Applied Phycology, vol. 3, 1991, pp. 247-257.

Maliakal et al., "Halogenated Monoterpene Production in Regenerated Plantlet Cultures of Ochtodes Secundiramea (Rhodophyta, Cryptonemiales)," Journal of Phycology, vol. 37, 2001, pp. 1010-1019.

Moon et al., "Isolation and characterization of thermostable phycocyanin from Galdieria sulphuraria," Korean Journal of Chemical Engineering, vol. 31, No. 3, 2014, pp. 490-495.

Muñoz et al., "Use of plant growth regulators in micropropagation of Kappaphycus alvarezii (Doty) in airlift bioreactors," Journal of Applied Phycology, vol. 18, 2006, pp. 209-218.

Perez et al., "Experimental Culture of the Brown Seaweed Undaria Pinnatifida Along the Coasts of France," Science et Péche, Bull. Inst. Pêches marit, vol. 343, Apr. 1984, pp. 3-16, with partial English translation provided.

Rorrer et al., "Production of Bioactive Metabolites By Cell and Tissue Cultures of Marine Macroalgae in Bioreactor Systems," Plant Cell and Tissue Culture for the Production of Food Ingredients, edited by Fu et al., Kluwer Academic / Plenum Publishers, New York, 1999, pp. 165-184.

Rusig et al., "Plant regeneration from protoplasts of Enteromorpha intestinalis (Chlorophyta, Ulvophyceae) as seedstock for macroagal culture," Journal of Applied Phycology, vol. 13, 2001, pp. 103-108.

Zhi et al., "Photolithotrophic cultivation of Laminaria saccharina gametophyte cells in a bubble-column bioreactor," Enzyme and Microbial Technology. vol. 18, No. 4, Mar. 1996, pp. 291-299.

* cited by examiner

METHOD FOR CULTURING CELLS OF *ACROCHAETIUM MONILIFORME* RED ALGAE, METHOD FOR OBTAINING AN EXTRACT OF THE BIOMASS THEREOF, AND USE OF SAME IN COSMETICS

The subject of the present invention is a novel extract of unialgal biomass of cells of small multicellular macroalgae, the method for preparing same and also the use thereof as a cosmetic active agent, and the cosmetic, pharmaceutical and dermo-pharmaceutical compositions for topical use comprising same.

Since human skin constitutes the first image provided to other people, improving the appearance thereof is often a preoccupying subject for human beings. The skin is the reflection either of a state of wellbeing, often associated with clear/radiant skin, or, on the contrary, of a state of fatigue and/or negligence, often associated with oily/shiny skin.

Oily skin is linked to a biological phenomenon known as hyperseborrhea or sebaceous hypersecretion, defined as being an abnormally high production of sebum by the sebaceous gland of the skin. This sebum, which flows at the surface of the skin, thus gives it this "shiny" unsightly characteristic. This hyperseborrhea is generally linked to an excess presence of the hormone testosterone which, once in the sebaceous gland, is converted by 5-alpha reductase into dihydrotestosterone (DHT), which binds to the receptors present in the sebaceous cells and activates sebum synthesis. Hyperseborrhea is accompanied by follicular hyperkeratinization, characterized by an increase in the number of keratinocytes in the follicular infundibulum, which causes an obstruction of the follicular canal and makes sebum flow difficult. This leads to an accumulation of sebum which is beneficial to the development of the anaerobic bacterium *Propionibacterium acnes*. The latter will cause the appearance of an inflammatory phenomenon. All of these phenomena result in the appearance of characteristic clinical signs, such as comedones, characterizing acneic skin.

Oily skin is thus a precursor state of the phenomenon of acne vulgaris, commonly called acne, which is an exclusively human, chronic inflammatory dermatosis of the pilosebaceous follicle. This pathological condition, which generally progresses by attacks, often begins at puberty and stops at the end of adolescence. However, even though 85% of young people from 12 to 24 years old are affected, requiring a specific and suitable treatment, 12% of women and 3% of men up to the age of 44 also have acne, or at the very least an acne-prone oily skin.

Since the sebaceous gland is annexed to the hair (reference is made to pilosebaceous follicle), the phenomena previously described can result in the state of an oily scalp and in the formation of visible clinical signs characterized as being oily dandruff.

"Dermopurifying" active ingredients can thus act on various phenomena:
Hyperseborrhea via agents that intervene, inter alia, on the amount of DHT;
Follicular hyperkeratinization via agents that limit, inter alia, keratinocyte differentiation;
Proliferation of *P. acnes* via agents, inter alia, of antibacterial/bacteriostatic nature.

The international application published under number WO 2008/046791 A1 discloses the use of 1,2-decanediol as an agent for decreasing sebum concentration on the skin and the advantage of this use compared with that of antibiotics such as tetracycline or of retinoids such as retinal or retinoic acid, for obtaining a satisfactory dermopurifying or anti-acne action.

These various agents have the drawbacks of being quite stressing for the skin, inducing skin reactions such as dryness, or else of not being effective enough.

Algae are photosynthetic chlorophyll organisms which live in water or in very moist environments. They can develop in seawater, fresh water, brine water, in stagnant, churned or turbulent environments. Algae can be unicellular or multicellular, they can be brown, green or red and are classified as a function of characteristics of cytological and biochemical order. These organisms play an important role on the global scale since they constitute the base of trophic networks and they are involved in the production of atmospheric oxygen and in the fixing of carbon dioxide.

Macroalgae are eukaryotic multicellular algae, usually visible to the naked eye and often described as macrophytes. They can reproduce sexually or asexually; in certain species, these two methods of reproduction follow on from one another during the life cycle. The life cycle can comprise one generation, or an alternating of two generations or of three generations. Reference will respectively be made to monogenetic, digenetic or trigenetic cycles.

Depending on the type of life cycle, the species can be in the form of gametophytes, sporophytes, carposporophytes or tetrasporophytes. During a cycle, these various life forms can be of the same morphologies and are therefore isomorphic, or of different morphologies and are therefore heteromorphic.

The difference in morphology may be very significant, making it impossible to attach two life forms to the same species for an uninformed person. This difference may also be marked due to the size of the algae, one life form may be macroscopic and another life form may be microscopic. For example, the sporophyte of *Undaria pinnatifida* measures close to one meter, whereas the gametophyte of this algae measures a few tens of micrometers.

There are approximately two thousand species of brown algae, seven thousand species of red algae and one thousand seven hundred species of green algae.

Macroalgae measure a few tens of micrometers in the case of the algae of the *Acrochaetium* genus to about a hundred meters for the *Macrocystis pyrifera* species.

The class of red algae, also called Florideophyceae, belongs to the rhodophyte branch. The class of red algae Florideophyceae comprises the orders Acrochaetiales, Acrosymphytales, Ahnfeltiales, Balbianiales, Balliales, Batrachospermales, Bonnemaisoniales, Ceramiales, Colaconematales, Corallinales, Entwisleiales, Florideophyceae incertae sedis, Gelidiales, Gigartinales, Gracilariales, Halymeniales, Hildenbrandiales, Nemaliales, Nemastomatales, Palmariales, Peyssonneliales, Pihiellales, Plocamiales, Rhodachlyales, Rhodogorgonales, Rhodymeniales, Sebdeniales, Sporolithales and Thoreales.

Red algae contain pigments encountered in the other plants, such as chlorophyll a and carotenoids, but their originality lies in the presence of phycobiliproteins: allophycocyanin (blue), phycocyanin (blue) and phycoerythrin which gives the red color. The organization of the chloroplasts differentiates the red algae from the glaucophytes and from the cyanobacteria.

The pigmentation of the red alga depends partly on the wavelength of the light that reaches the alga. At depth, the red algae accumulate a large amount of phycoerythrin, a pigment which can absorb light at this depth. At the surface, the ratio of the red pigment decreases, relative to chlorophyll and to the other phycobiliproteins, and they become greener despite their name; this is referred to as chromatic adaptation.

The Chinese patent application published under number CN 102475664 A discloses a cosmetic composition containing algal fibers for regulating sebum or pore contraction.

The red algae *Gelidium* and *Palmaria* are the most widely described for use as an agent regulating the oily skin condition. Thus, the Japanese patent application published under number P2005-47910 A discloses the use of various red algae, for example *Gelidium amansii, Gelidium japonica* and *Palmaria palmata*, for their sebum-secretion-inhibiting property, in cosmetics, in food or as a medicament. The Chinese patent application published under number CN 102525864 A discloses, for its part, the use of a peptide originating from seafood, coupled to algal polysaccharides from *Gelidium amansii*, and also to a pearl powder as anti-acne active agent. The Korean patent application published under number 2007 089309 discloses a method for preparing a *Gelidium amansii* concentrate, in order to obtain an oligosaccharide of a particular molecular size, having antimicrobial, antioxidant and anti-cancer properties.

However, the red algae of the orders Gelidiales and Palmariales are not known only for their dermopurifying properties. The Korean patent application published under number 10 1409764 A discloses the use of a *Gelidium amansii* extract having undergone a lactic fermentation process, as anti-wrinkle ingredient, that can be used in cosmetics or in nutrition. The French patent application published under number 2 911 278 discloses the use of a *Palmaria palmata* extract rich in sugar, as depigmenting cosmetic active agent.

Among the ten thousand different species of macroalgae, only about a hundred of them today provide an economic advantage. Thus, certain food microalgae, hydrocolloid-producing algae and algae producing molecules with biological activity have been the subject of extensive research in order to have a better understanding of their physiology, their metabolism and their reproduction.

The algae used in food for human consumption, such as *Undaria pinnatifida*, more commonly known as Wakame, *Laminaria japonica* also called Kombu, *Porphyra yezoensis*, also called Nori and *Enteromorpha intestinalis*, also called Ao nori, have been studied in order to master the culturing thereof.

The hydrocolloids produced by algae such as *Chondrus crispus, Kappaphycus* spp. and *Eucheuma denticulatum* are mainly used as thickeners and gelling agents in food and cosmetic products. The biomasses that produce these polymers are of definite economic interest [Ronelie C. et al. in: "Non-enzymatic isolation of somatic cells from *Kappaphycus* spp. and *Eucheuma denticulatum* (Solieriaceae, Rhodophyta)"; Eur. J. Phycol. (2014), 49(4): 486-492]. In this regard, Clinton J. Dawes et al. disclose a method for obtaining a unialgal biomass of cells of the red algae *Eucheuma denticulatum* and *Kappaphycus alvarezii*; from a sample taken from the natural environment, and the culture thereof for harvesting the biomass [Clinton J. Dawes et al. in: "Branch, micropropagule and tissue culture of the red algae *Eucheuma denticulatum* and *Kappaphycus alvarezii* farmed in the Philippines", Journal of applied Phycology 3: 247-257, 1991]. The same is true for Myounghoon et al. in the case of the red alga *Galdieria sulphuraria* [Myounghoon et al. in: "Isolation and characterization of thermostable phycocyanin from *Galdieria sulphuraria*", Korean J. Chem. Eng., 31(3), 490-495].

The culture in a bioreactor of the green alga *Acrosiphonia coalita*, the brown alga *Laminaria saccharina* and the red algae *Agardhiella subulata, Ochtodes secundiramea* and *Portieria hornemannii* has been studied with the aim of synthesizing molecules with biological activity [Gregory L. Rorrer et al. Production of bioactive metabolites by cell and tissue cultures of marine macroalgae in bioreactor systems. Plant Cell and Tissue Culture for the Production of Food Ingredients, edited by Fu et al. Kluwer Academic/Plenum Publishers, New York, 1999].

Some of them are based on knowledge and on the controlling of the reproductive cycle of the macroalga. For example, in laminariales, alternation between a macroscopic diploid sporophyte developed into a thallus and microscopic haploid male and female gametophytes can be observed. The mature fertile sporophytes produce swimming spores which become deposited on a solid substrate and which give rise to gametophytes. The study of their life cycle, such as that of *Undaria pinnatifida*, more commonly known as Wakame, or of *Laminaria japonica*, called Kombu, has made it possible to develop the culture of gametophytes, a microscopic life form of these algae, for seeding supports on which macroscopic sporophytes, that can be exploited in food for human consumption, develop. The culture of these algae is carried out firstly in a laboratory for the culture of the microscopic life form, and then in the natural environment for producing the macroscopic life form which may be consumed.

The development of the culture of the sporophyte of the brown algae of the order Laminariales, such as *Undaria pinnatifida*, in the 1980s, led to the development of a gametophyte culture technique known as "free living", which consists in harvesting mature sporophytes, bringing about sporulation, capturing the spores, forming gametophytes and then culturing them with the aim of creating gametes which, after fertilization, will give rise to new sporophytes (R. Perez et al., 1984).

The development of the culture of the *Laminaria saccharina* sporophyte also required the development of a method of culturing its gametophyte, in a manner similar to the *Undaria pinnatifida* cultures [C. Zhi, G. L. Rorrer. Photolithotrophic cultivation of *Laminaria saccharina* gametophyte cells in a bubble-column bioreactor. Enzyme and Microbial Technology. Volume 18, Issue 4, March 1996, Pages 291-299].

Likewise, for the purposes of experimental studies, H. Stegenga et al. isolated, by culturing samples of *Chromastrum moniliforme*, gametophytes and tetrasporophytes of these algae [H. Stegenga et al. in: "Remarks on the *Audouinella microscopica* (NÄG.) Woekerling complex, with a brief survey of the genus *chromastrum papenfuss (Rhodophyta, Nemaliales)*", Acta Bot. Neerl. 28(4/5), August 1979, p. 289-311].

The Chinese patent application published under number CN 103858745 A discloses the development of artificial cultures of *Scytosiphon lomentaria* by controlling the steps of differentiation of the germinative plasma of the alga, so as to produce a mature unilocular sporangium, then bringing about its sporulation with the aim of seeding culture supports for the purpose of producing, in the sea, biomass of macroscopic *Scytosiphon lomentaria*.

The Chinese patent application published under number CN 103931482 A discloses a method for obtaining a thallus of the gametophyte of the red alga *Porphyra yezoensis*, which is used in food for human consumption, in particular for maki, involving firstly the in vitro culture of the conchocelis phase of the alga in order to produce conchospores which will attach to a culture support so as to enable thallus growth in the sea.

Other methods involve the induction of calluses from explants of red algae, said calluses leading to the development of plantlets which are then cultured in a bioreactor. In this context, mention may be made of the studies by Ronelie et al. [Ronelie C. et al. Non-enzymatic isolation of somatic cells from *Kappaphycus* spp. and *Eucheuma denticulatum* (Solieriaceae, Rhodophyta), Eur. J. Phycol. (2014), 49(4): 486-492]; those of J. Munoz [J. Munoz. Use of plant growth regulators in micropropagation of *Kappaphycus alvarezii* (Doty) in airlift bioreactors. J Appl Phycol (2006) 18:209-218], or those of Maliakal et al. [S. Maliakal, D. Cheney. Halogenated monoterpenes production in regenerated plantlet cultures of *Ochtodes secundiramea*. J. Phycol. 37, 1010-1019 (2001)].

Other methods involve the production of protoplasts from a thallus with the aim of re-forming new thalluses, using, as proposed by Rusig et al. in the case of *Enteromorpha intestinalis*, an alga used in food for human consumption and animal feed, an enzymatic mixture containing cellulase and enzymes from aplysia which makes it possible to digest the wall of the algal thallus cells. The cultures of which the wall is digested are called protoplasts [A Rusig & J. Cosson, Plant regeneration from protoplasts of *Enteromorpha intestinalis* (Chlorophyta, Ulvophyceae) as seedstock for macroagal culture. Journal of Applied Phycology 13: 103-108, 2001].

Since small multicellular algae are not sufficiently abundant in nature to enable harvesting from the environment and their small size makes it difficult to identify the desired species and also to specifically harvest a given species, the inventors have endeavored to develop a novel method which makes it possible to obtain a unialgal biomass of cells of small multicellular macroalgae, in order to be able to extract therefrom an active ingredient that can be used in cosmetics.

They have developed a method that can be used in a bioreactor, which does not require having axenic explants and which does not involve phytohormones or enzymes.

According to a first aspect, a subject of the invention is a method for obtaining a unialgal biomass of cells of small multicellular macroalgae, comprising the following successive steps:

A step A) of preparing a unialgal sample of cells of multicellular macroalgae from a sample of macroalgae obtained from the natural environment;

A step B) of culturing said unialgal sample of cells of multicellular macroalgae obtained in step A) in seawater to which at least one nitrogen source has been added, in order to obtain an aqueous suspension of said unialgal biomass of cells of small multicellular macroalgae;

A step C) of harvesting said unialgal biomass of cells of small multicellular macroalgae from said aqueous suspension obtained at the end of step B);

A step D) of preparing a powder of said unialgal biomass of cells of small multicellular macroalgae obtained in step C).

The term "small multicellular macroalga" denotes, in the method as defined above, a multicellular macroalga measuring between 30 μm and 3 cm and organized in cell clumps. This small multicellular macroalga differs from a large multicellular macroalga since the latter measures between 5 cm and 20 cm and is organized in a tissue-like manner.

As sample of a macroalga taken from the natural environment, used in step A) of the method as defined above, in particular denoted is a sample taken from seawater, whether it is a sample of seawater, a sample taken at the surface of solid substrates such as rocks, sand, shells or sediments or else artificial supports such as the hull of a boat, a pontoon or a sea wall; it may also be a sample taken at the surface or from the inside of other plants (epiphyte or endophyte) such as algae or marine plants, or at the surface or on the inside of animals (epiphyte or endophyte) such as sponges, cnidaria, prochordates, echinoderms, molluscs, arthropods, annelids, or marine vertebrates.

The sample of macroalgae taken from the natural environment, used in step A) of the method as defined above, is generally very rich in biodiversity and contains a vast selection of living organisms such as small animals, protozoa, prokaryotic microalgae, eukaryotic microalgae and multicellular macroalgae.

The term "unialgal sample of cells of multicellular macroalgae", is intended to mean, in the method as defined above, a culture containing only one species of multicellular algae.

According to step A) of the method as defined above, the unialgal sample of cells of small multicellular macroalgae is obtained by isolating the macroalgae targeted from the other organisms the alga targeted. To this effect, physical separation means and/or chemical separation means can be implemented.

As physical separation means, there is for example separation carried out by means of a glass pipette using the end of the capillary to cut up a few cells of small multicellular macroalgae targeted, while controlling the operation visually, under a microscope or under a binocular magnifying lens. There is also separation by successive dilution of the cells of the targeted species from the natural sample.

As chemical separation means, there is for example the use of antibiotics to eliminate microalgae of the cyanobacteria type, or that of germanium dioxide to eliminate microalgae of the diatomaceous type.

The various isolation means are combined to obtain the best possible isolation result. All the physical and chemical isolation methods are carried out in translucent containers which allow light to pass through, containing sterile seawater, containing at least one nitrogen source such as sodium nitrate ($NaNO_3$) at a concentration of between 50 mg/dm$^3$ and 250 mg/dm$^3$ with a preference for 150 mg/dm$^3$ and a phosphorus source such as sodium dihydrogen phosphate ($NaH_2PO_4$) at a concentration of between 5 mg/dm$^3$ and 75 mg/dm$^3$ with a preference for 50 mg/dm$^3$.

It is also possible to add other mineral elements to the seawater, by adding, for example, a nutritive medium in the desired proportions, such as the Provasoli medium having the following composition:

| Provasoli medium | | | |
|---|---|---|---|
| $NaNO_3$ | 350 mg | $ZnSO_4 \cdot 7H_2O$ | 0.55 mg |
| sodium glycerophosphate | 50 mg | $CoSO_4 \cdot 7H2O$ | 0.12 mg |
| $Fe(NH_4)_2(SO_4)_2 \cdot 6H_2O$ | 18 mg | Vitamin B12 | 10 μg |
| $Na_2$ EDTA | 15 mg | Thiamine | 0.5 mg |
| $H_3BO_3$ | 28.5 mg | Biotin | 5 μg |
| $FeCl_3 \cdot 6H_2O$ | 1.225 mg | Tris buffer | 500 mg |
| $MnSO_4 \cdot H_2O$ | 4.1 mg | distilled water | 100 ml |

The implementation of step B) of the method as defined above is carried out in a photobioreactor containing seawater containing at least one nitrogen source such as sodium nitrate ($NaNO_3$) at a concentration of between 50 mg/dm$^3$ and 250 mg/dm³, with a preference for 150 mg/dm³, and a phosphorus source such as sodium dihydrogen phosphate (NaH$_2$PO$_4$) at a concentration of between 5 mg/dm³ and 75 mg/dm³, with a preference for 50 mg/dm³.

It is also possible to add other mineral elements to the seawater, by adding for example Provasoli medium in the desired proportions.

The cultures are carried out in translucent culture tanks with bubbling of air optionally enriched with carbon dioxide.

The cultures are generally carried out between 10° C. and 25° C. with a preference for 17° C., under constant illumination.

The cultures are carried out over periods of fifteen days in volumes ranging from 500 cm³ for the first culture steps up to 20 m³ for the industrial biomass production steps. However, when observations under a binocular magnifying lens and/or under a microscope carried out at the end of the first period of fifteen days demonstrate the growth of algae other than that targeted at the end of step A), this constitutes a sign that the result of step A) is not satisfactory. This step A) of the method as defined above is thus repeated until a unialgal sample of cells of small multicellular macroalgae of satisfactory quality is obtained.

Step C) of the method as defined above is generally carried out using a filter cloth with a cut-off threshold of between 25 µm and 100 µm depending on the size of the small multicellular macroalgae placed in culture. The culture of unialgal biomass of cells of small multicellular macroalgae is filtered, the seawater passing through the cloth and the biomass remaining at its surface. The retentate constituted by the biomass is then pressed in order to remove the free water still present.

Step D) of the method as defined above is carried out by methods known to those skilled in the art. It is possible for example to dry said unialgal biomass of cells of small multicellular macroalgae obtained in step C) of the method as defined above, and then to mill it and sieve it in order to obtain a powder having the desired mean diameter.

According to one particular aspect of the method as defined above, a subject thereof is a method for obtaining a unialgal biomass of cells of red algae from the class Florideophyceae, in the subclass Nemaliophycidae, of the order Acrochaetiales, of the genus *Acrochaetium* and of the species *Acrochaetium moniliforme*.

According to one particular aspect, during step D) of the method as defined above, said unialgal biomass of cells of small multicellular macroalgae obtained in step C) is frozen, lyophilized and then milled so as to obtain the desired powder.

A subject of the invention is also a method for preparing a glycolic extract of said unialgal biomass of cells of small multicellular macroalgae obtained by means of the process as defined above, characterized in that it comprises the following successive steps:

A step E) during which said unialgal biomass of cells of small multicellular macroalgae obtained in step C) or in step D) is dispersed with stirring in a water-glycol mixture in a proportion of 1% by weight to 20% by weight of biomass per 100% by weight of dispersion;

A step F) during which the dispersion obtained in step E) above is separated into its immiscible phases, so as to obtain the expected glycolic extract.

As glycol used in the method as defined above, there is in particular butylene glycol or 1,4-butanediol, 1,3-butanediol, 1,2-butanediol, 1,2-pentanediol, 1,5-pentanediol, 1,2-hexanediol or 1,6-hexanediol.

According to one particular aspect of the method as defined above, the glycol used is butylene glycol.

The water-to-glycol ratio by volume of the water/glycol mixture used in the method as defined above is generally less than or equal to 1/1 and greater than or equal to 1/9 and more particularly less than or equal to 1/2 and greater than or equal to 1/6. If necessary or if desired, this ratio by volume is adjusted within the abovementioned range at the end of step E).

According to one particular aspect of the method as defined above, a subject thereof is a method for preparing a glycolic extract of a unialgal biomass of cells of red algae from the class Florideophyceae, in the subclass Nemaliophycidae, of the order Acrochaetiales, of the genus *Acrochaetium* and of the species *Acrochaetium moniliforme*, obtained by means of the method as defined above, characterized in that it comprises the following successive steps:

A step E) during which the powder of said unialgal biomass of cells of red algae from the class Florideophyceae, in the subclass Nemaliophycidae, of the order Acrochaetiales, of the genus *Acrochaetium* and of the species *Acrochaetium moniliforme* obtained in step D) is dispersed with stirring in a water-butylene glycol mixture, the butylene glycol content by weight of which (ratio of weight of butylene glycol to total weight of butylene glycol and water) is between 50% and 75%, in a proportion of 2% by weight to 10% by weight of biomass per 100% by weight of dispersion; the stirring is maintained for one to two hours, and then if necessary or if desired the butylene glycol content by weight is adjusted to 40% by adding water;

A step F) during which the dispersion obtained in step E) above is separated into its immiscible phases, so as to obtain the expected glycolic extract.

During step F) of the method as defined above, the separation of the immiscible phases is carried out by decanting under gravity or by centrifugation.

If necessary or if desired, the hydroglycolic extract obtained is filtered through a filter with a cut-off threshold of 0.2 µm in order to remove any particle in suspension and to make it possible to obtain a clear solution.

A subject of the invention is thus a glycolic extract of a unialgal biomass of cells of small multicellular macroalgae obtained by means of the method comprising the following steps:

A step A) of preparing a unialgal sample of cells of small multicellular macroalgae, from a sample of macroalgae taken from the natural environment;

A step B) of culturing said unialgal sample of cells of small multicellular macroalgae obtained in step A) in seawater to which at least one nitrogen source has been added, in order to obtain an aqueous suspension of said unialgal biomass of cells of small multicellular macroalgae;

A step C) of harvesting said unialgal biomass of cells of small multicellular macroalgae from said aqueous suspension obtained at the end of step B);

Optionally, a step D) of preparing a powder of said unialgal biomass of cells of small multicellular macroalgae obtained in step C);

A step E) during which said unialgal biomass of cells of small multicellular macroalgae obtained in step C) or in step D) is dispersed with stirring in a water-glycol mixture in a proportion of 1% by weight to 20% by weight of biomass per 100% by weight of dispersion;

A step F) during which the dispersion obtained in step E) above is separated into its immiscible phases.

According to one particular aspect of the present invention, a subject thereof is the glycolic extract as defined above, in which the glycol used is butylene glycol.

According to another particular aspect of the present invention, a subject thereof is the glycolic extract as defined above, characterized in that the powder of said unialgal biomass of cells of small multicellular macroalgae used in step E) of the method for its preparation is a powder of said unialgal biomass of cells of red algae from the class Florideophyceae, in the subclass Nemaliophycidae, of the order Acrochaetiales, of the genus *Acrochaetium* and of the species *Acrochaetium moniliforme*.

According to one more particular aspect of the present invention, a subject thereof is the glycolic extract as defined above, characterized in that, during step E) of the method for its preparation:
the water-glycol mixture used is a water-butylene glycol mixture, the butylene glycol content by weight of which (ratio of weight of butylene glycol to total weight of butylene glycol and water) is between 50% and 75%,
the dispersion in said water-glycol mixture is carried out in a proportion of 2% by weight to 10% by weight of biomass per 100% by weight of dispersion; and
the stirring is maintained for one to two hours, and then if necessary or if desired,
the butylene glycol content by weight is adjusted to 40% by adding water.

A subject of the invention is also the use of the glycolic extract of a unialgal biomass of cells of small multicellular macroalgae as defined above, for the purpose of decreasing the amount of sebum produced by human skin and/or by the scalp, said use being in a cosmetic composition, and more particularly the use as defined above in which the glycolic extract of a unialgal biomass of cells of small multicellular macroalgae is the glycolic extract of a unialgal biomass of cells of red algae from the class Florideophyceae, in the subclass Nemaliophycidae, of the order Acrochaetiales, of the genus *Acrochaetium* and of the species *Acrochaetium moniliforme*, as defined above.

A subject of the invention is also a method for the purpose of decreasing the amount of sebum produced by human skin and/or by the scalp, comprising at least one step of applying, to said human skin and/or to said scalp, a cosmetic composition (C1) for topical use comprising at least one cosmetically acceptable excipient and an effective amount of the glycolic extract of a unialgal biomass of cells of small multicellular macroalgae as defined above; and more particularly a method as defined above, in which the glycolic extract of a unialgal biomass of cells of small multicellular macroalgae included in said composition (C1) is the glycolic extract of a unialgal biomass of cells of red algae from the class Florideophyceae, in the subclass Nemaliophycidae, of the order Acrochaetiales, of the genus *Acrochaetium* and of the species *Acrochaetium moniliforme*, as defined above.

By virtue of the ability to decrease the amount of sebum produced by human skin and/or by the scalp, the cosmetic compositions comprising said glycolic extract of red algae as defined above make it possible to treat condition-related skin modifications, termed oily skin, or condition-related hair modifications, termed greasy hair, by thus improving the esthetics.

A subject of the invention is also a cosmetic composition (C1), for topical use, comprising at least one cosmetically acceptable excipient and an effective amount of the glycolic extract of a unialgal biomass of cells of small multicellular macroalgae as defined above; and more particularly a composition (C1) as defined above in which the glycolic extract of a unialgal biomass of cells of small multicellular macroalgae is the glycolic extract of a unialgal biomass of cells of red algae from the class Florideophyceae, in the subclass Nemaliophycidae, of the order Acrochaetiales, of the genus *Acrochaetium* and of the species *Acrochaetium moniliforme*, as defined above.

In the method as defined above, said composition (C1) is generally spread over the surface of the skin to be treated and then the skin is massaged for a few moments.

The expression "for topical use" used in the definition of the composition (C1) which is the subject of the present invention means that said composition (C1) is used by application to the skin, whether it is direct application or indirect application when said composition (C1) according to the invention is impregnated onto a support intended to be brought into contact with the skin (paper, wipe, textile, transdermal device, etc.).

The expression "cosmetically acceptable" used in the definition of the composition (C1) which is the subject of the present invention means, according to European Economic Community Council Directive No. ° 76/768/EEC of 27 July, 1976, modified by directive No. ° 93/35/CEE of Jun. 14, 1993, that it comprises any substance or preparation intended to be brought into contact with the various parts of the human body (epidermis, body hair and head hair system, nails, lips and genital organs) or with the teeth and the mucous membranes of the oral cavity, with a view exclusively and mainly to cleaning them, perfuming them, changing their appearance and/or correcting body odors and/or protecting them or keeping them in good condition.

The term "effective amount of the glycolic extract of said unialgal biomass of cells of small multicellular macroalgae" as defined above is intended to mean, for 100% of the weight of said composition (C1), the amount of between 0.1% and 5% by weight, more particularly between 0.1% and 3% by weight, and even more particularly between 0.5% and 2% by weight of said glycolic extract of said unialgal biomass of cells of small multicellular macroalgae.

The composition (C1) which is a subject of the present invention is generally in the form of an aqueous or aqueous-alcoholic or aqueous-glycolic solution, or in the form of a suspension, an emulsion, a microemulsion or a nanoemulsion, whether it is of water-in-oil, oil-in-water, water-in-oil-in-water or oil-in-water-in-oil type, or in the form of a powder.

The composition (C1) which is a subject of the present invention can be packaged in a bottle, in a device of pump "dispenser bottle" type, in pressurized form in an aerosol device, in a device which has a perforated wall such as a grid, or in a device which has a ball applicator (termed "roll-on" device).

Generally, the glycolic extract of said unialgal biomass of cells of small multicellular macroalgae which is a subject of the present invention is combined with chemical additives normally used in the field of formulations for topical use, such as foaming and/or detergent surfactants, thickening and/or gelling surfactants, thickening and/or gelling agents, stabilizers, film-forming compounds, solvents and co-solvents, hydrotropic agents, spring or mineral waters, plasticizers, emulsifiers and co-emulsifiers, opacifiers, pearlescent agents, superfatting agents, sequestrants, chelating agents, oils, waxes, antioxidants, fragrances, essential oils, preservatives, conditioning agents, deodorants, whitening agents intended for bleaching body hairs and the skin, active ingredients intended to provide a treating and/or protective action with respect to the skin or the hair, sunscreens, mineral fillers or pigments, particles which provide a visual effect or are intended for the encapsulation of active agents, exfoliating particles, texturing agents, optical brighteners, or insect repellents.

As examples of foaming and/or detergent surfactants that can be combined with the glycolic extract of said unialgal biomass of cells of small multicellular macroalgae in the composition (C1), mention may be made of anionic, cationic, amphoteric or nonionic foaming and/or detergent surfactants.

Among the anionic foaming and/or detergent surfactants, mention may be made of the salts of alkali metals, of alkaline-earth metals, of ammonium, of amines or of amino alcohols, of alkyl ether sulfates, of alkyl sulfates, of alkylamido ether sulfates, of alkylaryl polyether sulfates, of monoglyceride sulfates, of alpha-olefin sulfonates, of paraffin sulfonates, of alkyl phosphates, of alkyl ether phosphates, of alkyl sulfonates, of alkylamide sulfonates, of alkylaryl sulfonates, of alkyl carboxylates, of alkyl sulfosuccinates, of alkylether sulfosuccinates, of alkylamide sulfosuccinates, of alkyl sulfoacetates, of alkyl sarcosinates, of acyl isethionates, of N-acyl taurates, of acyl lactylates, of N-acylated amino acid derivatives, of N-acylated peptide derivatives, of N-acylated protein derivatives, and of N-acylated fatty acid derivatives.

Among the amphoteric foaming and/or detergent surfactants, mention may be made of alkylbetaines, alkylamidobetaines, sultaines, alkylamidoalkylsulfobetaines, imidazoline derivatives, phosphobetaines, amphopolyacetates and amphopropionates.

Among the cationic foaming and/or detergent surfactants, mention may in particular be made of quaternary ammonium derivatives.

Among the nonionic foaming and/or detergent surfactants, mention may be made more particularly of alkylpolyglycosides comprising a linear or branched, saturated or unsaturated aliphatic radical and comprising from 8 to 16 carbon atoms, such as octyl polyglucoside, decyl polyglucoside, undecylenyl polyglucoside, dodecyl polyglucoside, tetradecyl polyglucoside, hexadecyl polyglucoside or 1,12-dodecanediyl polyglucoside; ethoxylated derivatives of hydrogenated castor oil such as the product sold under the INCI name "Peg-40 hydrogenated castor oil"; polysorbates such as Polysorbate 20, Polysorbate 40, Polysorbate 60, Polysorbate 70, Polysorbate 80 or Polysorbate 85; coconut amides; N-alkylamines.

As examples of thickening and/or gelling surfactants that can be combined with the glycolic extract of said unialgal biomass of cells of small multicellular macroalgae in the composition (C1), mention may be made of optionally alkoxylated alkylpolyglycoside fatty esters, for instance ethoxylated methylpolyglucoside esters such as PEG 120 methyl glucose trioleate and PEG 120 methyl glucose dioleate sold respectively under the names Glucamate™ LT and Glumate™ DOE120; alkoxylated fatty esters such as PEG 150 pentaerythrytyl tetrastearate sold under the name Crothix™ DS53, PEG 55 propylene glycol oleate sold under the name Antil™ 141; fatty-chain polyalkylene glycol carbamates, for instance PPG-14 laureth isophoryl dicarbamate sold under the name Elfacos™ T211 or PPG-14 palmeth-60 hexyl dicarbamate sold under the name Elfacos™ GT2125.

As examples of thickening and/or gelling agents that can be combined with the glycolic extract of said unialgal biomass of cells of small multicellular macroalgae in the composition (C1), mention may be made of linear or branched or crosslinked polyelectrolyte-type polymers, for instance partially or totally salified acrylic acid homopolymers, partially or totally salified methacrylic acid homopolymer, partially or totally salified 2-methyl-[(1-oxo-2-propenyl)amino]-1-propanesulfonic acid (AMPS) homopolymer, copolymers of acrylic acid and of AMPS, copolymers of acrylamide and of AMPS, copolymers of vinylpyrolidone and of AMPS, copolymers of AMPS and of (2-hydroxyethyl) acrylate, copolymers of AMPS and of (2-hydroxyethyl) methacrylate, copolymers of AMPS and of hydroxyethylacrylamide, copolymers of AMPS and of N,N-dimethyl acrylamide, copolymers of AMPS and of tris (hydroxymethyl)acrylamidomethane (THAM), copolymers of acrylic acid or methacrylic acid and of (2-hydroxyethyl) acrylate, copolymers of acrylic or methacrylic acid and of (2-hydroxyethyl) methacrylate, copolymers of acrylic or methacrylic acid and of hydroxyethylacrylamide, copolymers of acrylic or methacrylic acid and of THAM, copolymers of acrylic or methacrylic acid and of N,N-dimethylacrylamide, terpolymers of acrylic or methacrylic acid, of AMPS and of (2-hydroxyethyl) acrylate, terpolymers of acrylic or methacrylic acid, of AMPS and of (2-hydroxyethyl) methacrylate, terpolymers of acrylic or methacrylic acid, of AMPS and of THAM, terpolymers of acrylic or methacrylic acid, of AMPS and of N,N-dimethyl acrylamide, terpolymers of acrylic or methacrylic acid, of AMPS and of acrylamide, copolymers of acrylic acid or of methacrylic acid and of alkyl acrylates of which the carbon-based chain comprises between four and thirty carbon atoms and more particularly between ten and thirty carbon atoms, copolymers of AMPS and of alkyl acrylates of which the carbon-based chain comprises between four and thirty carbon atoms and more particularly between ten and thirty carbon atoms, linear, branched or crosslinked terpolymers of at least one monomer having a strong acid function which is free, partially salified or totally salified, with at least one neutral monomer, and at least one monomer of formula (VIII):

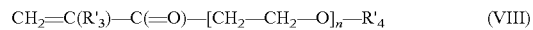

$$CH_2=C(R'_3)-C(=O)-[CH_2-CH_2-O]_n-R'_4 \qquad (VIII)$$

in which $R'_3$ represents a hydrogen atom or a methyl radical, $R'_4$ represents a linear or branched alkyl radical comprising from eight to thirty carbon atoms and n represents a number greater than or equal to one and less than or equal to fifty.

The linear or branched or crosslinked polyelectrolyte-type polymers that can be combined with the glycolic extract of said unialgal biomass of cells of small multicellular macroalgae in the composition (C1) can be in the form of a solution, of an aqueous suspension, of a water-in-oil emulsion, of an oil-in-water emulsion, or of a powder. The linear or branched or crosslinked polyelectrolyte-type polymers that can be combined with the glycolic extract of said unialgal biomass of cells of small multicellular macroalgae in the composition (C1) can be selected from the products sold under the names Simulgel™ EG, Simulgel™EPG, Sepigel™ 305, Simulgel™ 600, Simulgel™ NS, Simulgel™ INS 100, Simulgel™ FL, Simulgel™ A, Simulgel™ SMS 88, Sepinov™EMT 10, Sepiplus™400, Sepiplus™265, Sepiplus™S, Sepimax™Zen, Aristoflex™AVC, Aristoflex™AVS, Novemer™EC-1, Novemer™EC 2, Aristoflex™HMB, Cosmedia™SP, Flocare™ET 25, Flocare™ET 75, Flocare™ET 26, Flocare™ET 30, Flocare™ET 58, Flocare™PSD 30, Viscolam™AT 64, Viscolam™AT 100.

As examples of thickening and/or gelling agents that can be combined with the glycolic extract of said unialgal biomass of cells of small multicellular macroalgae in the composition (C1), mention may be made of polysaccharides consisting only of monosaccharides, for instance glucans or homopolymers of glucose, glucomannoglucans, xyloglycans, and galactomannans of which the degree of substitution (DS) of the D-galactose units on the main D-mannose chain is between 0 and 1, and more particularly between 1 and 0.25, for instance galactomannans originating from cassia gum (DS=1/5), locust bean gum (DS=1/4), tara gum (DS=1/3), guar gum (DS=1/2) or fenugreek gum (DS=1).

As examples of thickening and/or gelling agents that can be combined with the glycolic extract of said unialgal biomass of cells of small multicellular macroalgae in the composition (C1), mention may be made of polysaccharides consisting of monosaccharide derivatives, for instance sulfated galactans and more particularly carrageenans and agar, uronans and more particularly algins, alginates and pectins, heteropolymers of monosaccharides and of uronic acids and more particularly xanthan gum, gellan gum, gum arabic exudates and karaya gum exudates, or glucosaminoglycans.

As examples of thickening and/or gelling agents that can be combined with the glycolic extract of said unialgal biomass of cells of small multicellular macroalgae in the composition (C1), mention may be made of cellulose, cellulose derivatives such as methylcellulose, ethylcellulose or hydroxypropylcellulose, silicates, starch, hydrophilic starch derivatives, and polyurethanes.

As examples of stabilizers that can be combined with the glycolic extract of said unialgal biomass of cells of small multicellular macroalgae in the composition (C1), mention may be made of microcrystalline waxes, and more particularly ozokerite, mineral salts such as sodium chloride or magnesium chloride, and silicone polymers such as polysiloxane polyalkyl polyether copolymers.

As examples of solvents that can be combined with the glycolic extract of said unialgal biomass of cells of small multicellular macroalgae in the composition (C1), mention may be of water, organic solvents such as glycerol, diglycerol, glycerol oligomers, ethylene glycol, propylene glycol, butylene glycol, 1,3-propanediol, 1,2-propanediol, hexylene glycol, diethylene glycol, xylitol, erythritol, sorbitol, water-soluble alcohols such as ethanol, isopropanol or butanol, and mixtures of water and of said organic solvents.

As examples of spring water or mineral water that can be combined with the glycolic extract of said unialgal biomass of cells of small multicellular macroalgae in the composition (C1), mention may be made of spring water or mineral water having a mineralization of at least 300 mg/l, in particular Avene water, Vittel water, Vichy basin water, Uriage water, La Roche-Posay water, La Bourboule water, Enghien-les-Bains water, Saint-Gervais-les Bains water, Neris-les-bains water, Allevard-les-Bains water, Digne water, Maizieres water, Neyrac-les-Bains water, Lons-le-Saunier water, Rochefort water, Saint Christau water, Les Fumades water and Tercis-les-Bains water.

As examples of hydrotropic agents that can be combined with the glycolic extract of said unialgal biomass of cells of small multicellular macroalgae in the composition (C1), mention may be made of xylene sulfonates, cumene sulfonates, hexyl polyglucoside, (2-ethylhexyl) polyglucoside or n-heptyl polyglucoside.

As examples of emulsifying surfactants that can be combined with the glycolic extract of said unialgal biomass of cells of small multicellular macroalgae in the composition (C1), mention may be made of nonionic surfactants, anionic surfactants and cationic surfactants.

As examples of emulsifying nonionic surfactants that can be combined with the glycolic extract of said unialgal biomass of cells of small multicellular macroalgae in the composition (C1), mention may be made of fatty acid esters of sorbitol, for instance the products sold under the names Montane™40, Montane™60, Montane™70, Montane™80 and Montane™85; compositions comprising glyceryl stearate and stearic acid ethoxylated between five mol and one hundred and fifty mol of ethylene oxide, for instance the composition comprising stearic acid ethoxylated with one hundred and thirty-five mol of ethylene oxide and glyceryl stearate sold under the name Simulsol™ 165; mannitan esters; ethoxylated mannitan esters; sucrose esters; methyl glucoside esters; alkyl polyglycosides comprising a linear or branched, saturated or unsaturated aliphatic radical and comprising from fourteen or thirty-six carbon atoms, for instance tetradecyl polyglucoside, hexadecyl polyglucoside, octadecyl polyglucoside, hexadecyl polyxyloside, octadecyl polyxyloside, eicosyl polyglucoside, dodecosyl polyglucoside, (2-octyldodecyl) polyxyloside, (12-hydroxystearyl) polyglucoside; compositions of linear or branched, saturated or unsaturated fatty alcohols, comprising from fourteen to thirty-six carbon atoms, and of alkyl polyglycosides as described above, for example the compositions sold under the trade names Montanov™68, Montanov™14, Montanov™82, Montanov™202, Montanov™S, Montanov™WO18, Montanov™L, Fluidanov™20X and Easynov™.

As examples of anionic surfactants that can be combined with the glycolic extract of said unialgal biomass of cells of small multicellular macroalgae in the composition (C1), mention may be made of glyceryl stearate citrate, cetearyl sulfate, soaps such as sodium stearate or triethanolammonium stearate, salified N-acylated amino acid derivatives, for instance stearoyl glutamate.

As examples of emulsifying cationic surfactants that can be combined with the glycolic extract of said unialgal biomass of cells of small multicellular macroalgae in the composition (C1), mention may be made of aminoxides, quaternium-82 and the surfactants described in patent application WO 96/00719 and mainly those of which the fatty chain comprises at least sixteen carbon atoms.

As examples of opacifiers and/or pearlescent agents that can be combined with the glycolic extract of said unialgal biomass of cells of small multicellular macroalgae in the composition (C1), mention may be made of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate, and fatty alcohols comprising from twelve to twenty-two carbon atoms.

As examples of texturing agents that can be combined with the glycolic extract of said unialgal biomass of cells of small multicellular macroalgae in the composition (C1), mention may be made of N-acylated amino acid derivatives, such as lauroyl lysine sold under the name Aminohope™LL, octenyl starch succinate sold under the name Dryflo™, myristyl polyglucoside sold under the name Montanov™ 14, cellulose fibers, cotton fibers, chitosan fibers, talc, sericite and mica.

As examples of deodorants that can be combined with the glycolic extract of said unialgal biomass of cells of small multicellular macroalgae in the composition (C1), mention may be made of alkali metal silicates, zinc salts such as zinc sulfate, zinc gluconate, zinc chloride or zinc lactate; quaternary ammonium salts such as cetyltrimethylammonium salts or cetylpyridinium salts; glycerol derivatives such as glyceryl caprate, glyceryl caprylate or polyglyceryl caprate; 1,2-decanediol; 1,3-propanediol; salicylic acid; sodium bicarbonate; cyclodextrins; metal zeolites; Triclosan™; aluminum hydrobromide, aluminum hydrochlorides, aluminum chloride, aluminum sulfate, aluminum zirconium hydrochlorides, aluminum zirconium trihydrochloride, aluminum zirconium tetrahydrochloride, aluminum zirconium pentahydrochloride, aluminum zirconium octohydrochloride, aluminum sulfate, sodium aluminum lactate, complexes of aluminum hydrochloride and of glycerol, such as the complex of aluminum hydrochloride and of propylene glycol, the complex of aluminum dihydrochloride and of propylene glycol, the complex of aluminum sesquihydrochloride and of propylene glycol, the complex of aluminum hydrochloride and of polyethylene glycol, the complex of aluminum dihydrochloride and of polyethylene glycol, or the complex of aluminum sesquihydrochloride and of polyethylene glycol.

As examples of oils that can be combined with the glycolic extract of said unialgal biomass of cells of small multicellular macroalgae in the composition (C1), mention may be made of mineral oils such as liquid paraffin, liquid petroleum jelly, isoparaffins or white mineral oils; oils of animal origin, such as squalene or squalane; vegetable oils, such as phytosqualane, sweet almond oil, coconut oil, castor oil, jojoba oil, olive oil, rapeseed oil, groundnut oil, sunflower oil, wheatgerm oil, corn germ oil, soybean oil, cottonseed oil, alfalfa oil, poppy oil, pumpkin oil, evening primrose oil, millet oil, barley oil, rye oil, safflower oil, candlenut oil, passionflower oil, hazelnut oil, palm oil, shea butter, apricot kernel oil, beauty-leaf oil, sysymbrium oil, avocado oil, calendula oil, oils derived from flowers or vegetables, ethoxylated vegetable oils; synthetic oils, for instance fatty acid esters such as butyl myristate, propyl myristate, isopropyl myristate, cetyl myristate, isopropyl palmitate, octyl palmitate, butyl stearate, hexadecyl stearate, isopropyl stearate, octyl stearate, isocetyl stearate, dodecyl oleate, hexyl laurate, propylene glycol dicaprylate, lanolic acid-based esters, such as isopropyl lanolate, isocetyl lanolate, monoglycerides, diglycerides and triglycerides of fatty acids, such as glyceryl triheptanoate, alkyl benzoates, hydrogenated oils, poly(alpha-olefins), polyolefins such as poly (isobutane), synthetic isoalkanes such as isohexadecane, isododecane, perfluoro oils; silicone oils such as dimethylpolysiloxanes, methylphenyl polysiloxanes, silicones modified with amines, silicones modified with fatty acids, silicones modified with alcohols, silicones modified with alcohols and fatty acids, silicones modified with polyether groups, modified epoxy silicones, silicones modified with fluoro groups, cyclic silicones and silicones modified with alkyl groups. The term "oils" is intended to mean, in the present application, compounds and/or mixtures of compounds that are insoluble in water, and that have a liquid appearance at a temperature of 25° C.

As examples of waxes that can be combined with the glycolic extract of said unialgal biomass of cells of small multicellular macroalgae in the composition (C1), mention may be made of beeswax, carnauba wax, candelilla wax, ouricury wax, Japan wax, cork fiber wax, sugar cane wax, paraffin waxes, lignite waxes, microcrystalline waxes, lanolin wax; ozokerite; polyethylene wax; silicone waxes; plant waxes; fatty alcohols and fatty acids that are solid at ambient temperature; glycerides that are solid at ambient temperature. In the present application, the term "waxes" is intended to mean compounds and/or mixtures of compounds that are insoluble in water and that have a solid appearance at a temperature greater than or equal to 45° C.

As examples of active ingredients that can be combined with the glycolic extract of said unialgal biomass of cells of small multicellular macroalgae in the composition (C1), mention may be made of vitamins and derivatives thereof, in particular esters thereof, such as retinol (vitamin A) and esters thereof (retinyl palmitate for example), ascorbic acid (vitamin C) and esters thereof, sugar derivatives of ascorbic acid (such as ascorbyl glucoside), tocopherol (vitamin E) and esters thereof (such as tocopheryl acetate), vitamins B3 or B10 (niacinamide and derivatives thereof); compounds which show lightening or depigmenting action on the skin, such as w-undecylenoyl phenylalanine sold under the name Sepiwhite™MSH, Sepicalm™VG, the glycerol monoester and/or diester of w-undecylenoyl phenylalanine, w-undecylenoyl dipeptides, arbutin, kojic acid, hydroquinone; compounds showing a soothing action, in particular Sepicalm™ S, allantoin and bisabolol; anti-inflammatories; compounds showing a moisturizing action, such as urea, hydroxyureas, glycerol, polyglycerols, glycerolglucoside, diglycerolglucoside, polyglycerylglucosides, xylitylglucoside, the composition sold under the trade name Aquaxyl™, the composition sold under the trade name Pro-Xylane™, C-glycoside derivatives and more particularly C-glucoside or C-xyloside derivatives; polyphenol-rich plant extracts, such as grape extracts, pine extracts, wine extracts, olive extracts; compounds showing a slimming or lipolytic action, such as caffeine or derivatives thereof, Adiposlim™, Adipoless™, fucoxanthin; N-acylated proteins; N-acylated peptides, such as Matrixil™; N-acylated amino acids; partial hydrolyzates of N-acylated proteins; amino acids; peptides; total protein hydrolyzates; soybean extracts, for example Raffermine™; wheat extracts, for example Tensine™ or Gliadine™; plant extracts, such as tannin-rich plant extracts, isoflavone-rich plant extracts or terpene-rich plant extracts; extracts of freshwater or seawater algae; marine plant extracts; marine extracts in general, such as corals; essential waxes; bacterial extracts; ceramides; phospholipids; compounds showing an antimicrobial action or a purifying action, such as Lipacide™ C8G, Lipacide™ UG, Sepicontrol™ A5, Fluidipure™8G; Octopirox™ or Sensiva™ SC50; compounds showing an energizing or stimulating property, such as Physiogenyl™, panthenol and derivatives thereof, such as Sepicap™ MP; anti-aging active agents, such as Sepilift™ DPHP, Lipacide™ PVB, Sepivinol™, Sepivital™, Manoliva™, Phyto-Age™, Timecode™; Survicode™; anti-photoaging active agents; active agents for protecting the integrity of the dermoepidermal junction; active agents for increasing the synthesis of extracellular matrix components such as collagen, elastins, glycosaminoglycans; active agents which act favorably on chemical cell communication, such as cytokines, or physical cell communication, such as integrins; active agents which create a "heating" sensation on the skin, such as skin microcirculation activators (such as nicotinic acid derivatives) or products which create a feeling of "coolness" on the skin (such as menthol and derivatives); active agents for improving skin microcirculation, for example veinotonics; draining active agents; active agents for decongestive purposes, such as extracts of ginko biloba, of ivy, of horse chestnut, of bamboo, of ruscus, of butcher's broom, of *Centalla asiatica*, of fucus, of rosemary, of willow; agents for tanning or browning the skin, such as dihydroxyacetone (DHA), erythrulose, mesotartric aldehyde, glutaraldehyde, glyceraldehyde, alloxane, ninhydrin, plant extracts, for example extracts of red woods of the *Pterocarpus* genus and of the *Baphia* genus, such as *Pterocarpus santalinus, Pterocarpus osun, Pterocarpus soyauxii, Pterocarpus erinaceus, Pterocarpus indicus* or else *Baphia nitida*, such as those described in European patent application EP 0 971 683; agents known for their action in facilitating and/or accelerating the tanning and/or browning of the human skin and/or for their action in coloring the human skin, for example the carotenoids (and more particularly beta-carotene and gamma-carotene), the product sold under the name "carrot oil" (INCI name: *Daucus Carota, helianthis annuus* sunflower oil) by Provital, which contains carotenoids, vitamin E and vitamin K; tyrosine and/or derivatives thereof, known for their effect in accelerating the tanning of the human skin in combination with exposure to ultraviolet radiation, for example the product sold under the trade name "Sun Tan Accelerator™" by Provital which contains tyrosine and riboflavins (vitamin B), the complex of tyrosine and tyrosinase sold under the trade name "Zymo Tan Complex" by Zymo Line, the product sold under the trade name MelanoBronze™ (INCI name: Acetyl Tyrosine, Monk's pepper extract (Vitex agnus-castus)) by Mibelle which contains acetyl tyrosine, the product sold under the trade name Unipertan VEG-24/242/2002 (INCI name: butylene glycol and Acetyl Tyrosine and hydrolyzed vegetable protein and Adenosine triphosphate) by UNIPEX, the product sold under the trade name "Try-Excell™" (INCI name: Oleoyl Tyrosine and *Luffa Cylindrica* (Seed) Oil and Oleic acid) by Sederma which contains extracts of marrow seeds (or Loofah oil), the product sold under the trade name "Actibronze™" (INCI name: hydrolyzed wheat protein and acetyl tyrosine and copper gluconate) by Alban Muller, the product sold under the trade name Tyrostan™ (INCI name: potassium caproyl tyrosine) by Synerga, the product sold under the trade name Tyrosinol (INCI name: Sorbitan Isostearate, glyceryl oleate, caproyl Tyrosine) by Synerga, the product sold under the trade name InstaBronze™ (INCI name: Dihydroxyacetone and acetyl tyrosine and copper gluconate) sold by Alban Muller, the product sold under the trade name Tyrosilane (INCI name: methylsilanol and acetyl tyrosine) by Exymol; peptides known for their effect of activation of melanogenesis, for example the product sold under the trade name Bronzing SF Peptide powder (INCI name: Dextran and Octapeptide-5) by Infinitec Activos, the product sold under the trade name Melitane (INCI name: Glycerin and Aqua and Dextran and Acetyl hexapeptide-1) comprising acetyl hexapeptide-1 known for its alpha-MSH agonist action, the product sold under the trade name Melatimes Solutions™ (INCI name: Butylene glycol, Palmitoyl Tripeptide-40) by LIPOTEC, sugars and sugar derivatives, for example the product sold under the trade name Tanositol™ (INCI name: inositol) by Provital, the product sold under the trade name Thalitan™ (or Phycosaccharide™ AG) by CODIF international (INCI name: Aqua and hydrolyzed algin (*Laminaria digitata*) and magnesium sulfate and manganese sulfate) containing an oligosaccharide of marine origin (guluronic acid and mannuronic acid chelated with magnesium and manganese ions), the product sold under the trade name Melactiva™ (INCI name: Maltodextrin, *Mucuna Pruriens* Seed extract) by Alban Muller, flavonoid-rich compounds, for example the product sold under the trade name "Biotanning" (INCI name: Hydrolyzed citrus *Aurantium dulcis* fruit extract) by Silab and known to be rich in lemon flavonoids (of hesperidin type); agents intended for treating head hair and/or body hair, for example agents which protect the melanocytes of the hair follicle, intended to protect said melanocytes against cytotoxic agents which are responsible for the senescence and/or apoptosis of said melanocytes, such as mimetics of dopachrome tautomerase activity, chosen from those described in the European patent application published under the number EP 1 515 688 A2, synthetic SOD mimetic molecules, for example manganese complexes, antioxidant compounds, for example cyclodextrin derivatives, siliceous compounds derived from ascorbic acid, lysine or arginine pyrrolidonecarboxylate, combinations of mono- and diesters of cinnamic acid and of vitamin C, and more generally those mentioned in the European patent application published under the number EP 1 515 688 A2.

As examples of antioxidants that can be combined with the glycolic extract of said unialgal biomass of cells of small multicellular macroalgae in the composition (C1), mention may be made of EDTA and salts thereof, citric acid, tartaric acid, oxalic acid, BHA (butylhydroxyanisole), BHT (butylhydroxytoluene), tocopherol derivatives, such as tocopheryl acetate, mixtures of antioxidant compounds such as Dissolvine™ GL 47S sold by the company Akzo Nobel under the INCI name: Tetrasodium Glutamate Diacetate.

As examples of sunscreens that can be combined with the glycolic extract of said unialgal biomass of cells of small multicellular macroalgae in the composition (C1), mention may be made of all those which are included in the amended cosmetics directive 76/768/EEC, annexe VII.

Among the organic sunscreens that can be combined with the glycolic extract of said unialgal biomass of cells of small multicellular macroalgae in the composition (C1), mention may be made of the family of benzoic acid derivatives, such as para-aminobenzoic acids (PABAs), especially monoglyceryl esters of PABA, ethyl esters of N,N-propoxy PABA, ethyl esters of N,N-diethoxy PABA, ethyl esters of N,N-dimethyl-PABA, methyl esters of N,N-dimethyl-PABA, butyl esters of N,N-dimethyl-PABA; the family of anthranilic acid derivatives, such as homomenthyl-N-acetyl anthranilate; the family of salicylic acid derivatives, such as amyl salicylate, homomenthyl salicylate, ethylhexyl salicylate, phenyl salicylate, benzyl salicylate, or p-isopropanolphenyl salicylate; the family of cinnamic acid derivatives, such as ethylhexyl cinnamate, ethyl 4-isopropyl cinnamate, methyl 2,5-diisopropyl cinnamate, propyl p-methoxycinnamate, isopropyl p-methoxycinnamate, isoamyl p-methoxycinnamate, octyl p-methoxycinnamate, 2-ethylhexyl p-methoxycinnamate, 2-ethoxyethyl p-methoxycinnamate, cyclohexyl p-methoxycinnamate, ethyl α-cyano-3-phenylcinnamate, 2-ethylhexyl α-cyano-β-phenylcinnamate, mono(2-ethylhexanoyl)glyceryl di(para-methoxycinnamate); the family of benzophenone derivatives, such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octyloxybenzophenone, 4-hydroxy-3-carboxybenzophenone; 3-(4'-methylbenzylidene)-d,l-camphor, 3-(benzylidene)-d,l-camphor, camphor benzalkonium methosulfate; urocanic acid, ethyl urocanate; the family of sulfonic acid derivatives, such as 2-phenylbenzimidazole-5 sulfonic acid and salts thereof; the family of triazine derivatives, such as hydroxyphenyl triazine, ethylhexyloxyhydroxyphenyl-4-methoxyphenyltriazine, 2,4,6-trianillino-(p-carbo-2'-ethylhexyl-1'-oxy)-1,3,5-triazine, benzoic acid 4,4-((6-(((1,1-dimethylethyl)amino) carbonyl)phenyl)amino)-1,3,5-triazine-2,4-diyl diimino) bis (2-ethylhexyl) ester, 2-phenyl-5-methylbenzoxazole, 2,2'-hydroxy-5'-methylphenylbenzotriazole, 2-(2'-hydroxy-5'-t-octylphenyl)benzotriazole, 2-(2'-hydroxy-5'-methylphenyl) benzotriazole; dibenzazine; dianisoylmethane, 4-methoxy-4"-t-butylbenzoylmethane; 5-(3,3-dimethyl-2-norbornylidene)-3-pentan-2-one; the family of diphenyl acrylate derivatives, such as 2-ethylhexyl-2-cyano-3,3-diphenyl-2-propenoate, ethyl-2-cyano-3,3-diphenyl-2-propenoate; the family of polysiloxanes, such as benzylidene siloxane malonate.

Among the inorganic sunscreens, also called "mineral sunscreens", that can be combined with the glycolic extract of said unialgal biomass of cells of small multicellular macroalgae in the composition (C1), mention may be made of titanium oxides, zinc oxides, cerium oxide, zirconium oxide, yellow, red or black iron oxides, and chromium oxides. These mineral sunscreens may or may not be micronized, may or may not have undergone surface treatments and may be optionally present in the form of aqueous or oily predispersions.

A subject of the invention is also the glycolic extract of said unialgal biomass of cells of small multicellular macroalgae as defined above, for the use thereof in a therapeutic treatment method aimed at reducing the amount of sebum produced by human skin and/or by the scalp, and more particularly the glycolic extract of a unialgal biomass of cells of red algae from the class Florideophyceae, in the subclass Nemaliophycidae, of the order Acrochaetiales, of the genus *Acrochaetium* and of the species *Acrochaetium moniliforme*, as defined above, for the use thereof in a therapeutic treatment method aimed at reducing the amount of sebum produced by human skin and/or by the scalp.

The following examples illustrate the invention without however limiting it.

Samples Tested to Show the Technical Effect

Extract A: Glycolic extract (in butylene glycol) of a culture of the alga *Acrochaetium moniliforme* obtained by means of the method according to the invention Extract B: Glycolic extract (in butylene glycol) of the alga *Delesseria* obtained from a lyophilisate of biomass of said alga;

Extract C: Glycolic extract (in butylene glycol) of the alga *Palmaria* obtained from a lyophilisate of biomass of said alga;

Extract D: Glycolic extract (in butylene glycol) of the alga *Gelidium* obtained from a lyophilisate of biomass of said alga.

Biological Efficacy

Choice of the Model and Relevance:

The model chosen to demonstrate the technical effect of our products is a model for studying the production of dihydrotestosterone (DHT), revealing the activity of the 5-α-reductase enzyme, an enzyme that is highly targeted for determining the dermopurifying properties of cosmetic ingredients. This model is a cellular model, that is more robust than models on purified enzyme.

Protocol:

Human fibroblasts of the dermal follicular papilla (man, 22 years old) were seeded into collagen-coated culture plates in the presence of a specific growth medium. After three days, they were pretreated for 24 hours with the positive reference [Finasteride (F) at 2 µM and 1 µM] and each of the algal extracts to be tested (Table 2). The fibroblasts were then stimulated with testosterone at 0.5 µM before undergoing a post-treatment for 24 hours. Each test was carried out in sextuplicate.

TABLE 2

| Product | Concentrations tested |
| --- | --- |
| Extract A | 0.5% and 0.1% |
| Extract B | 0.5% and 0.1% |
| Extract C | 0.5% and 0.1% |
| Extract D | 0.5% and 0.1% |

Evaluation of the Effects:

The viability was measured using a WST-8 reagent and the conversion of the testosterone was then evaluated by measuring the intracellular concentration of (DHT). The viability was expressed relative to that of the control without testosterone (control T0). The amount of (DHT) was standardized relative to the viability results and then related to the control condition with testosterone (0.5 µM) control (T1) in order to calculate a percentage effect, and also related to the control conditions without testosterone in order to calculate a percentage protection.

Results:

The DHT production results are presented in Table 3 below.

TABLE 3

Results regarding DHT production

| | WST-8 | | DHT Concentration (pg/ml) | Standardized concentration (pg/ml/AU) | Effect | Restoration |
| --- | --- | --- | --- | --- | --- | --- |
| Product | OD (AU) | Viability | | | | |
| (T0) | 2.26 +/− 0.15[a] | 100% | 6.97 +/− 1.32[a] | 3.09 +/− 0.54[a] | −61%*[a] | 100% |
| | 2.18 +/− 0.09[b] | | 11.74 +/− 2.29[b] | 5.30 +/− 0.80[b] | −30%*[b] | |
| | 2.01 +/− 0.19[c] | | 5.75 +/− 0.73[c] | 2.86 +/− 0.40[c] | −72%*[c] | |
| (T1) | 2.14 +/− 0.19[a] | 95%[a] | 16.85 +/− 2.28[a] | 7.85 +/− 0.67[a] | 0% | 0% |
| | 2.21 +/− 0.25[b] | 110%[b] | 16.54 +/− 1.68[b] | 7.53 +/− 0.93[b] | | |
| | 1.89 +/− 0.09[c] | 94%[c] | 15.38 +/− 6.14[c] | 10.12 +/− 4.82[c] | | |
| (F) (2 µM) | 2.19 +/− 0.27[a] | 93%[a] | 12.38 +/− 2.35[a] | 5.68 +/− 0.91[a] | −28%* | 46%* |
| A (0.5%) | 2.24 +/− 0.10[a] | 100% | 11.18 +/− 3.5[a] | 5.03 +/− 1.71[a] | −36%* | 59%* |
| A (0.1%) | 2.14 +/− 0.14[a] | 95% | 8.89 +/− 3.01[a] | 4.17 +/− 1.28[a] | −47%* | 77%* |
| B (0.5%) | 2.05 +/− 0.33[c] | 102% | 9.64 +/− 1.33[c] | 4.59 +/− 0.29[c] | −55%[LS] | 76%[LS] |
| B (0.1%) | 2.10 +/− 0.17[c] | 105% | 19.89 +/− 10.38[c] | 9.21 +/− 5.01[c] | −9% | 13% |
| C (0.5%) | 2.33 +/− 0.26[b] | 116%* | 16.26 +/− 6.22[b] | 7.02 +/− 2.67[b] | −7% | 23% |
| C (0.1%) | 2.34 +/− 0.17[b] | 116%* | 15.79 +/− 3.81[b] | 6.82 +/− 1.94[b] | −9% | 32% |
| D (0.5%) | 2.24 +/− 0.17[b] | 111%* | 14.93 +/− 1.92[b] | 6.89 +/− 0.92[b] | −8% | 28% |
| D (0.1%) | 2.20 +/− 0.16[b] | 109%* | 13.01 +/− 4[b] | 6.01 +/− 2.10[b] | −20% | 68% |

[a], [b] and [c] set of experiments
*statistically significant results (Student's test, p < 0.05)
[LS] results close to statistical significance (Student's test, 0.05 < p < 0.1)

The extracts A (extracts of an *Acrochaetium moniliforme* biomass, obtained according to the method of the invention) showed a limiting effect on DHT production, close to a basal layer. These effects attest to a sebum-production-regulating activity and thus a cosmetic activity characterized as "dermopurifying".

The compounds B (conventional extract of *Delesseria*), C (conventional extract of *Palmaria*) and D (conventional extract of *Gelidium*) did not show any significant effect on DHT production (except a slight effect of the compound B at the highest concentration).

The method of the invention makes it possible to obtain an extract which has a dermopurifying effect that is more advantageous/differentiating than the other red algae, the dermopurifying properties of which have already been described.

Formulations

In the following examples, the proportions are expressed as weight percentages.

| Dermopurifying oil-in-water emulsion | |
|---|---|
| Water | qs 100% |
| Glycerol | 3% |
| Solagum ™AX | 0.3% |
| Montanov ™202 | 2% |
| Lanol ™ 99 | 7% |
| Cetiol ™OE | 3% |
| Lanol ™P | 0.25% |
| Sepiplus ™400 | 0.8% |
| Euxyl ™PE9010 | 1% |
| Sensiva ™PA40 | 0.5% |
| Extract A | 1% |
| Lactic acid at 20% | qs pH = 5.5 |

| Anti-sebum oil-in-water emulsion | |
|---|---|
| Water | qs 100% |
| Montanov ™202 | 3% |
| Montanov ™14 | 1.5% |
| Pelemol ™BB | 2% |
| Shea butter | 1.5% |
| Phytosqualane | 3% |
| Jojoba oil | 3% |
| C8-C10 triglyceride | 3% |
| DUB ISIP | 3% |
| D,L-α-tocopherol | 0.1% |
| Solagum ™Tara | 0.6% |
| Extract A | 2% |
| Sorbic acid | 0.3% |
| 48% sodium hydroxide | 0.07% |

| Soothing serum | |
|---|---|
| Sepimax ™Zen | 0.5% |
| Water | qs 100% |
| Butylene glycol | 2% |
| Aquaxyl ™ | 2% |
| Extract A | 1% |
| Montanox 20 | 1% |
| Phenoxyethanol & Ethylhexyl Glycerin | 0.80% |

Solagum™AX: Mixture of acacia gum and xanthan gum used as emulsifying agent and sold by the company SEPPIC;
Montanov™202 (INCI name: Arachidyl Alcohol & Behenyl Alcohol & Arachidyl Glucoside): Emulsifying agent sold by the company SEPPIC;
Lanol™ 99: Isononyl isononanoate sold by the company SEPPIC;
Cetiol™OE (INCI name: Dicaprylyl ether): Fatty phase sold by the company BASF;
Lanol™ P: Glycol palmitate sold by the company SEPPIC;
Sepiplus™400 (INCI name: Polyacrylate-13 & Polyisobutene & Polysorbate 20): Polymeric thickening agent sold by the company SEPPIC;
Euxyl™PE9010 (INCI name: phenoxyethanol and ethylhexylglycerin): Preservative sold by the company Schilcke & Mayr;
Sensiva™PA40 (INCI name: Phenethyl Alcohol (and) Ethylhexylglycerin): Antimicrobial agent sold by the company Schilcke & Mayr;
Montanov™14 (INCI name: Myristyl Alcohol & Myristyl Glucoside): Emulsifying agent sold by the company SEPPIC;
Pelemol™BB/Behenyl Behenate sold by the company Phoenix Chemical;
Solagum™Tara: Tara gum used as emulsifying agent and sold by the company SEPPIC;
Sepimax™Zen (INCI name: polyacrylate crosspolymer-6): Thickening, emulsifying and stabilizing agent;
Aquaxyl™ (INCI name: Xylitylglucoside and Anhydroxylitol and Xylitol): Moisturizing composition sold by the company SEPPIC;
Montanox™ 20 (INCI name: Polysorbate 20): Emulsifying agent of oil-in-water type sold by the company SEPPIC.

The invention claimed is:

1. A method for preparing a glycolic extract of a unialgal biomass of cells of small multicellular macroalgae, wherein the microalgae is Acrochaetium moniliforme, comprising the following steps:
    A) preparing a unialgal biomass of cells of small multicellular macroalgae from a sample of macroalgae;
    B) culturing said unialgal biomass of cells of multicellular macroalgae obtained in step A) in seawater to which at least one nitrogen source has been added to obtain an aqueous suspension of said unialgal biomass of cells of small multicellular macroalgae;
    C) harvesting said cultured unialgal biomass of cells of small multicellular macroalgae from said aqueous suspension obtained in step B);
    D) preparing a powder of said cultured unialgal biomass of cells of small multicellular macroalgae obtained in step C);
    E) dispersing the powder of said cultured unialgal biomass of cells of small multicellular macroalgae obtained in step D) in a water-glycol mixture by stirring 1% by weight to 20% by weight of the biomass based on the weight of the water-glycol mixture; and
    F) separating the glycolic extract from the dispersion of step E).

2. The method of claim 1, wherein the glycol is butylene glycol.

3. The method of claim 1, wherein in step E):
    the water-glycol mixture is a water and butylene glycol mixture;
    the amount of butylene glycol is between 50% by weight and 75% by weight based on the total weight of the water-butylene glycol mixture;
    the weight of the biomass is 2% by weight to 10% by weight of biomass; and
    stirring is maintained for one to two hours.

4. The method of claim 1, wherein the powder is prepared by freezing, lyophilizing, and milling the cultured unialgal biomass of cells of small multicellular macroalgae from step C).

* * * * *